United States Patent [19]

Le Boeuf

[11] 4,320,001
[45] Mar. 16, 1982

[54] LIQUID FILTER HAVING REFINED VENT VALVE

[76] Inventor: Guy Le Boeuf, 9 rue Aristide Briand, Cormeilles en Parisis, France, 95240

[21] Appl. No.: 149,738

[22] Filed: Mar. 14, 1980

[30] Foreign Application Priority Data

May 17, 1979 [FR] France ................. 79 12619

[51] Int. Cl.³ ............................................ B01D 35/14
[52] U.S. Cl. ................................... 210/120; 210/123; 210/136; 210/436; 210/472
[58] Field of Search ....... 210/436, 120, 472, DIG. 23, 210/188, 123, 136; 128/214 R, 214 C; 55/170; 422/45, 46; 137/433, 202

[56] References Cited

U.S. PATENT DOCUMENTS 4,009,714  3/1977  Hammer .................. 128/214 C X
4,126,558  11/1978  Luceyk ..................... 210/436 X
4,190,426  2/1980  Ruschke ................... 210/436 X

FOREIGN PATENT DOCUMENTS 465486  9/1928  Fed. Rep. of Germany ........ 55/170

*Primary Examiner*—Frank A. Spear, Jr.
*Attorney, Agent, or Firm*—Holman & Stern

[57] ABSTRACT

A device for filtering a liquid, provided with a chamber for the circulation of liquid, divided into at least two compartments by a filtering-unit mounted across the liquid path. That device comprises, in an area where the air present in the liquid or separated therefrom has accumulated, a one-way valve for exhausting air, should any overpressure take place in that area. The valve is provided with an obturator integral with a float driven by the free level of the liquid. That obturator cooperates with two opposed valve-seats for closing a passage made in the wall of the filtration chamber.

11 Claims, 6 Drawing Figures

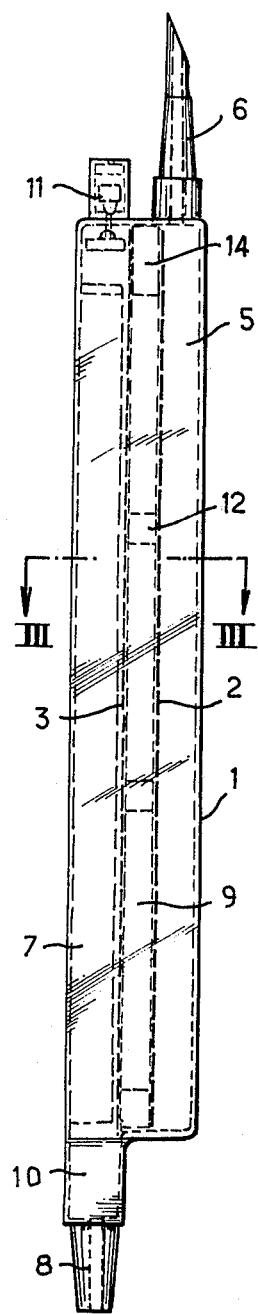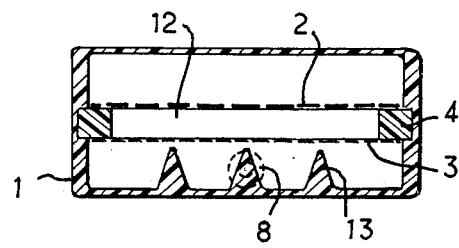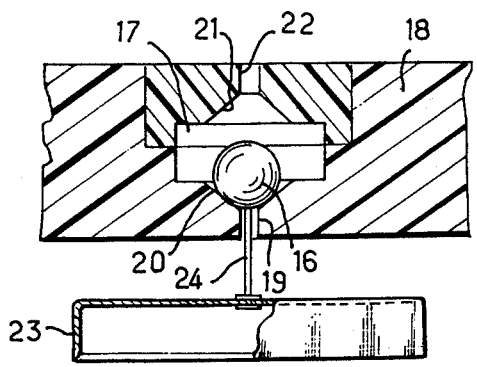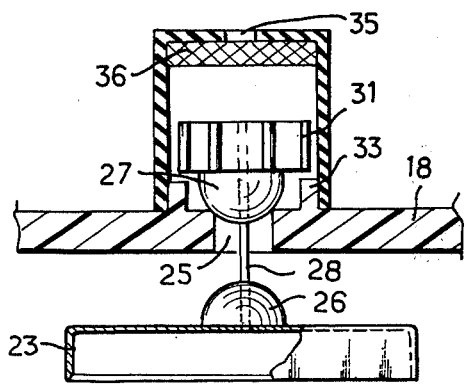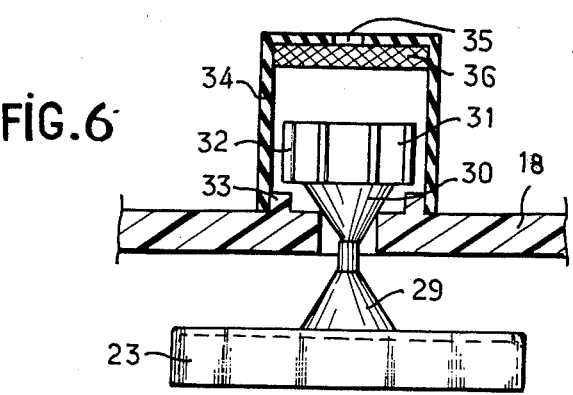

LIQUID FILTER HAVING REFINED VENT VALVE

BACKGROUND OF THE INVENTION

1. Field of the Invention

The present invention relates to filtration devices and more especially those to be used for filtering physiological fluids in medical treatments. Its object is to provide a filtration device, the design of which is such that it is, in particular, more suitable than the devices of the prior art, for filtering blood in blood-transfusion installations, e.g. those in operating-rooms.

2. Discussion of the Prior Art

Filters used in installations of that kind should be adapted to be readily and rapidly mounted in the blood-circuit feeding the injection-needle, and they should be of such a low price that they can be disposed of after use. Such filters, however, must allow the user, so long as they are being utilized, to adjust at will the fluid flow-rate within a range that, in some cases, may happen to be very wide. To this end, it is imperative, in particular, to prevent the filter from becoming choked up, which would be likely to obstruct the blood-circulation area within a short time and would unduly reduce the blood flow-rate. Moreover, care must be taken to avoid the penetration of air into the circulating blood, resulting in the injection of air-filled blood into the veins of the patient under treatment.

It is, in fact, the usual practice in blood-transfusion installations, to provide the circuit feeding the injection syringe both with a filter adapted to retain solid materials and with an air-trap for retaining air bubbles. But in such cases, normally two different devices are involved, whereas, in the present invention, the above two functions are combined in a single device, in a single and highly efficient way not only allowing the safe retention of the air-bubbles, but permitting, in addition, the separation of any amount of air contingently mixed with the blood and the retention of same.

SUMMARY OF THE INVENTION

The device according to the invention, adapted to filtering a liquid (e.g. blood in transfusion installations) comprises a chamber for the circulation of liquid with a filtering unit mounted across the liquid path for retaining solid substances, and, in addition, in an area where the air present in said chamber has accumulated (and also any amount of air possibly carried by said liquid and separated therefrom during the filtering step), a one-way valve which ensures the exhaust of air should any over-pressure take place in said area, the obturator of said valve being connected to a float which acts to close the valve by being lifted by the liquid when the level of the latter comes up to near the valve.

The above-mentioned chamber forms an elongated container for the vertical circulation of the liquid to be filtered (e.g. blood) between an inlet connecting member protruding from the container top and an outlet connecting member protruding from the bottom of said container. These two connecting members are laterally arranged on both sides of a filtering unit comprising at least one sieve adapted to divide said container vertically along the full height thereof.

The valve of the device according to the invention is then preferably mounted in the container top portion, in the outlet compartment, i.e. on that side of the filtering unit opposite to the liquid inlet connecting member. This is where air is accumulated, opposite the selective sedimentation receivers, constituted by the container lower portion (the number of which depends on the number of sieves in the filtering unit), when said container gradually fills up the free level of the liquid rising gradually as clogging of the filtering unit increases upwards.

According to a preferred embodiment of the filtering device according to the invention, the filtering unit contains a plurality of sieves (from two to eight), arranged vertically within the container while horizontally spaced, the diameters of the cavities, or holes, in said sieves varying gradually from one sieve to the next one. In view of such an arrangement, the circulation of fluid is still improved and, above all, through an effect of selective sedimentations, the particles that tend to clog up the various sieves are distributed according to their sizes, thus permitting considerable extension of the life of the sieve without having to increase the height of the device, unduly.

In actual practice, the container of the device according to the invention can be given quite a number of shapes; the most simple embodiment comprises flat sieves in a container of cylindrical or parallelepipedic shape; however, it may prove preferable to make use of cylindrical sieves connected with either the fluid inlet or the fluid outlet, one of which is arranged along the device axis, the other being mounted in the vicinity of the container periphery. Quite obviously, a plurality of fluid inlets and/or outlets can be provided, all such inlets, on the one hand, and all such outlets, on the other hand, being similarly arranged with respect to the filtering unit. In any case, it is preferable that each inlet be directed vertically but shifted laterally with respect to the sieves, or other filters, in order to prevent blood from dripping directly on said sieves.

In every variant of the filtering device according to the invention relating to the particular mounting of the filtering unit and of the valve and to their respective positions, said valve essentially fulfills three functions. In the particular instance of the filtration of blood, first, the valve allows air to escape from the container to the atmosphere whenever blood is flowing through the filter, in view of the fact that any overpressure of air in the accumulation area causes the valve to open; secondly, the valve prevents atmospheric air (of course, non sterile) from penetrating into the container whenever the latter is in a state of underpressure with respect to the outside, which may occur, e.g. when the circulation of blood is obtained by means of a peristaltic pump, mounted downstream of the filter; thirdly, and finally, the valve prevents blood from being expelled from the device when the container is about to be filled with blood. The device according to the present invention thus permits elimination of any trace of air present in the blood more thoroughly than with an air-trap mounted downstream of the filter; the device according to the invention also prevents the air separated in the filter from being trapped at the top of the latter and sufficiently compressed to be mixed with the blood and driven further therewith; it also prevents the formation of an air pocket which would reduce the container capacity and diminish the filtering power of the device.

According to further features of the present invention, the above described three functions are preferably fulfilled by a valve comprising a double-acting obturator cooperating with two oppositely-mounted valve seats for closing a passage way through a filtration chamber wall, whenever there exists the absence of any gas overpressure within said chamber. The obturator rests on a first one of said seats, on the one hand, and whenever, because of the pressure exerted by the liquid, said obturator is caused to rise beyond an open position of the valve until it is applied against the second one of said seats, on the other hand.

The liquid thrust is transmitted to the obturator by the integral float adapted to be driven by the liquid free level when said free level is in the vicinity of the valve.

BRIEF DESCRIPTION OF THE DRAWINGS

Other features of the present invention, regarding both the valve proper and further details on the filtering device on which said valve is mounted, will appear from the following description, given merely by way of example, with reference to the accompanying drawing, in which:

FIG. 2 is a lateral view of the filter of FIG. 1;

FIG. 3 shows the same filter, in cross-section along line III—III of FIG. 1;

FIG. 4 is a detailed view of a first embodiment of the valve;

FIG. 5 is a partial cross-section of a second embodiment of the valve; and

FIG. 6 shows a third embodiment of a valve to be used on the filter of FIG. 1.

DESCRIPTION OF THE PREFERRED EMBODIMENTS

Figure 1:
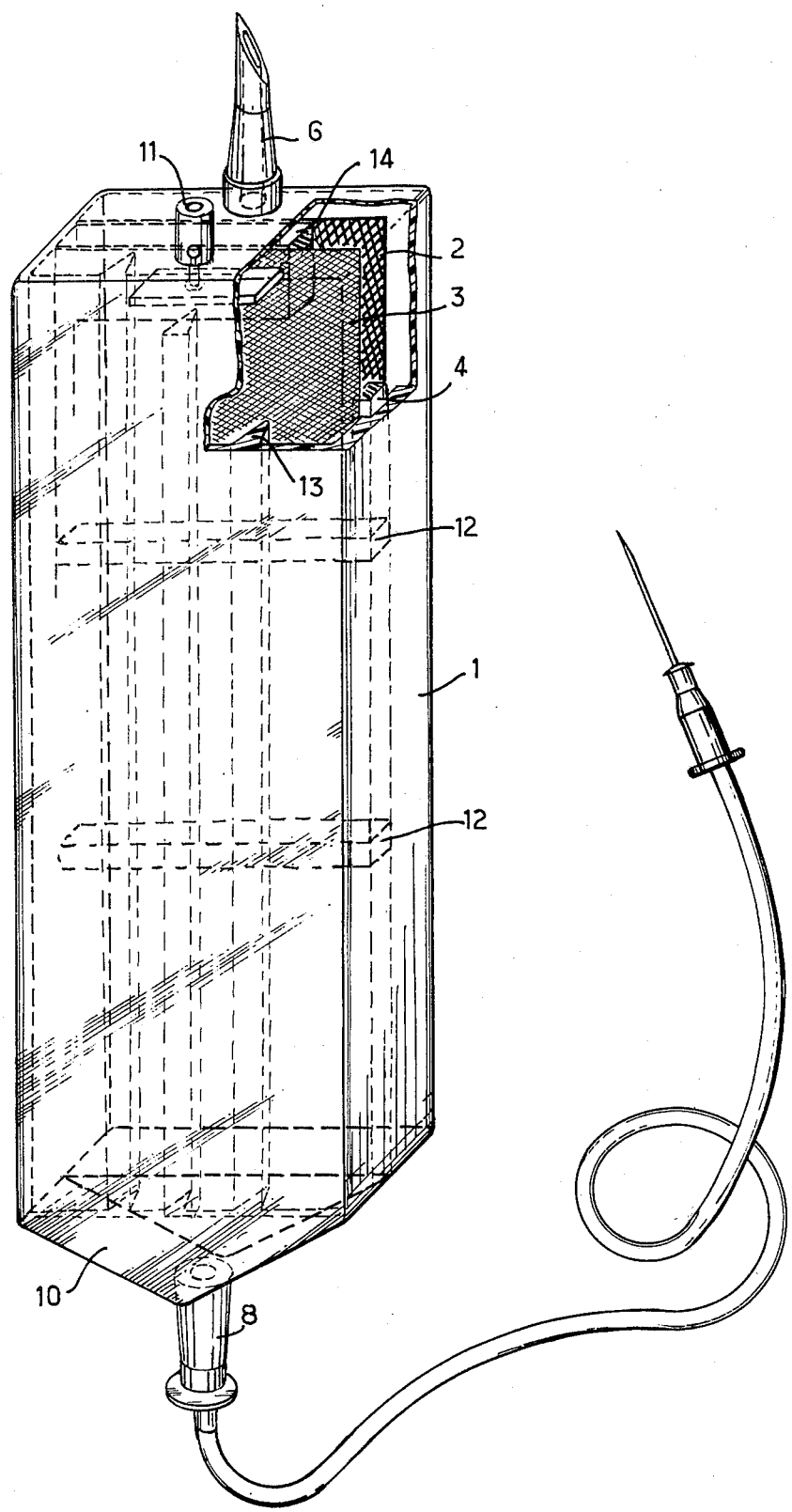
FIG. 1 is a partially exploded general view of a blood-filter according to the present invention.

The filter as described, more specifically intended for the treatment of human blood in transfusion equipment, is defined by a container 1 enclosing an elongated parallelepipedic chamber (shown in FIGS. 1 and 2 such as it appears during use, viz. with its major dimension vertically arranged). This container, along the whole length thereof, is divided by a filtering unit, comprising two filter-sieves 2 and 3 in the specific embodiment shown. These sieves are carried by a rigid frame 4, engaged in grooves made in the lateral surfaces of container 1 and they are vertically arranged in spaced parallel relationship.

Said sieves 2 and 3 longitudinally divide container 1 into, first, a blood inlet compartment 5, into which opens a feed connecting-member 6, vertically protruding from the device upper surface; secondly, a blood outlet compartment 7, into which opens an outlet connecting-member 8, vertically protruding from the device bottom-surface; and, thirdly, an intermediate compartment 9 defined by compartments 5 and 7. A multipurpose valve 11 is mounted on the device at the top of outlet compartment 7, in a vertical opening through the upper surface of container 1. Both sieves are attached (by means of an adhesive or through a re-moulding operation) to the outer surfaces of frame 4. The holes, or perforations, in sieve 2, located next to inlet compartment 5, are larger than those of sieve 3, located next to outlet compartment 7. Frame 4 is provided with crosspieces 12 adapted to maintain the two sieves in spaced relationship; and in order to prevent fine-meshed sieve 3 from being damaged under the action of any unduly high thrust of the liquid passing through the two sieves, the inner surface of the wall of compartment 7 is provided with longitudinal fins. At the filter bottom, the lower surface of container 1 closes compartments 5 and 9 by a flat bottom, whereas, under outlet compartment 7, said lower surface is extended and downwardly tapered until it meets connecting-member 8, thus forming a blood-collecting bottom portion 10.

In operation, the outlet duct is connected to an injection needle as shown in FIG. 1 and blood is fed to the inlet either by gravity or by pumping at a flow rate regulated to compensate for the withdrawal flow rate. A free level of blood is allowed to form at an intermediate level within container 1, so that any air present separates from the blood while dust and impurities are retained by the sieves, with a selective effect depending on the particle size. The blood level may be different in different compartments between adjacent sieves. More than two sieves may be used, for instance up to five, with respective mesh diameters of 400, 200, 100, 50, 25 micrometers and spaced by 4 millimeters from each other. The blood level becomes gradually higher while clogging of the sieves advances upwards. However an optimum filtering efficiency is obtained and the pressure drop stands at a low value while the device is in use.

With regard to the filter construction at the upper portion thereof, it is to be noted that, in the middle area, fins 13 do not reach the top of container 1 so as not to interfere with valve 11, whereas the upper side of frame 4 has been designed high enough thus avoiding too direct a communication through the sieves at that level where, in use, blood is introduced into compartment 5 of the device, while any amount of air possibly driven by the blood collects in the upper portion of compartment 7.

A description will now be given of the three embodiments of valve 11, with reference to FIGS. 4, 5, 6. In each of said variants, valve 11 is provided with a double-acting obturator, cooperating with two opposed seats in the wall defining the filtration chamber, for closing the passageway provided in that wall between said wall and the atmosphere whenever said obturator, adapted to reciprocate vertically, is at one of two extreme positions, whereas said passageway is open when the obturator is at an intermediate position. In addition, said obturator is permanently integral with a float adapted to be raised by the liquid whenever the liquid free level reaches the float.

According to FIG. 4, the obturator is constituted by a spherical member, or ball, 16 retained in a housing 17 provided inside wall 18 forming the upper side of container 1. Along the periphery of an opening 19 through which housing 17 is in communication with compartment 7 of container 1, said housing is defined by a conical area constituting a first seat 20 for ball 16. An oppositely tapered conical seat 21 is formed all around an opening 22 through which housing 17 is in communication with the atmosphere. A rectangular hollow float 23 hangs from ball 16. It is integrally connected to it by a rod 24 coaxially passing through conduit 19 without obturating the latter.

It will be easily understood that, in use, the obturator constituted by ball 16 is normally in contact with lower seat 20, under the action of its own weight plus the weight of float 23, whereas, when the air-overpressure at the top of compartment 7 is high enough to compensate for the weight of the obturator, ball 16 is caused to rise from its seat, thus allowing air to escape through conduits 19 and 22.

On the other hand, in case of negative pressure in the filter, ball 16 is, of course, applied against seat 20, still more firmly then under normal conditions.

However, whenever the free level of the blood filling up the filter rises high enough for driving float 23 therewith, ball 16 then is raised together with said float but it obstructs the communication with the atmosphere by being applied against upper seat 21, and the blood cannot flow out of the container.

In the embodiment of FIG. 5, the two obturator seats are constituted by the very edges of a passageway 25 provided through wall 18, these edges being each on a respective side of that wall, and the obturator proper comprises two portions on either side of wall 18, said two portions being mutually connected in passageway 25. In FIG. 5, these two obturator portions are in the shape of half-spheres 26, 27 connected by a rod 28. Float 23, similar to that of FIG. 4, is welded to half-sphere 26. The functions of the two seats are interchanged with respect to FIG. 4: in the absence of a gas overpressure, half-sphere 27 closes the valve along the upper seat, whereas lower half-sphere 26 is applied against the lower seat as a result of a thrust exerted by the liquid through float 23.

In the embodiment shown in FIG. 6, the operation is similar to that of FIG. 5, the only difference lying in the obturator shape, the two half-spheres 26 and 27 being exchanged for cones 29, 30, respectively, said cones being oppositely arranged at their apex. Moreover, both in FIG. 5 and in FIG. 6, the obturator upper portion (27, 30) is topped by a cylindrical head 31, provided with vertical ribs 32. During the normal valve operation, head 31 is moved vertically together with the obturator, above an annular protrusion 33 of wall 18. Around said protrusion is mounted a cylindrical guide-member 34, of a flexible material, surmounting valve-head 31, without interfering with the normal operation of the latter. Guide-member 34 is closed at the top thereof, except for an orifice, or port 35, for the passage of air when the valve is open. Said orifice is covered by a bacteriological filter 36, mounted inside guide-member 34.

Guide-member 34 is flexible enough to allow the user to reach valve-head 31 with the hand, merely by deforming said guide-member. Such a possibility is resorted to after the filter has been used, following a blood transfusion operation, for fully draining the filter of any remaining blood by allowing atmospheric air to enter through the valve. In order to release the obturator from its seat, the operator has merely to push sidewards with a finger the head 31 which protrudes from wall 18 inside flexible guide-member 34. Contingently, the obturator is also capable of rocking, when head 31 is caused to rest along a side thereof on annular protrusion 33.

Quite obviously, various changes can be made in the above described valves without going beyond the scope of the present invention. In particular, the above embodiments can be combined in various ways so as to provide further variants; moreover, modifications of detail may be made in the design of both the sieves and the filtering unit.

What is claimed is:

1. A device for filtering a physiological liquid, comprising a chamber for the circulation of said liquid, a filtering unit mounted across the liquid path through said chamber and dividing said chamber into at least two compartments and a one-way valve for the exhaust of overpressure air from a top part of said chamber, said valve being provided with an obturator integral with a float, said float positioned within said chamber and adapted to be lifted by a free level of said liquid in the vicinity of the valve, the said obturator cooperating with two opposed valve-seats for closing a passageway through the filtration chamber wall, in the absence of any gas-overpressure inside said chamber and under the thrust exerted by said liquid driving said float, whenever said free level is in the vicinity of said valve, respectively.

2. A device according to claim 1, wherein said obturator is integral with a head mounted outside said filtration chamber, for manual operation of said valve.

3. A device according to claim 2, further comprising a protecting resilient guide-member covering said head outside said chamber.

4. A device according to claim 3, wherein said resilient guide-member contains a bacteriological filter adapted to shield an opening, or port, for the passage of air.

5. A device according to claim 1, wherein said obturator comprises two mutually integral portions, each of which is situated on one side of the wall of said filtration chamber, the said opposed valve-seats being constitued, on either side of said wall, by the respective end edges of said passage.

6. A device according to claim 1, wherein the said filtration chamber constitutes an elongated container for the vertical flow of said liquid, in which said filtering unit comprises at least one vertical sieve, and wherein the said valve is arranged at the top of that compartment through which said liquid is drained from said device.

7. A device according to claim 6, wherein are provided means for preventing the said liquid from flowing directly through said sieve, at the level of said air-accumulation area.

8. A device according to claim 6, wherein the compartment through which said liquid is drained is provided with a liquid-collecting bottom portion.

9. A device according to claim 1, wherein said filtering unit comprises a frame and at least one sieve mounted in said frame.

10. A device according to claim 9, wherein said frame is vertically mounted and said at least one sieve comprises a plurality of sieves positioned in parallel spaced relationship to one another across the liquid path and each sieve of said plurality of sieves has progressively smaller openings than the adjacent preceding sieve.

11. A device according to claim 9, wherein said plurality of sieves comprises two sieves.

* * * * *

UNITED STATES PATENT AND TRADEMARK OFFICE
CERTIFICATE OF CORRECTION

PATENT NO. : 4,320,001
DATED : March 16, 1982
INVENTOR(S) : GUY LE BOEUF

It is certified that error appears in the above-identified patent and that said Letters Patent are hereby corrected as shown below:

ON THE TITLE PAGE,

[22] Filed: Mar. 14, 1980

Should be

--[22] Filed: May 14, 1980--

*Signed and Sealed this*

*Twentieth Day of July 1982*

[SEAL]

*Attest:*

*Attesting Officer*

GERALD J. MOSSINGHOFF

*Commissioner of Patents and Trademarks*